United States Patent [19]

Brawner et al.

[11] Patent Number: 4,717,666
[45] Date of Patent: Jan. 5, 1988

[54] CLONED STREPTOMYCETE LIVIDANS EXCRETABLE β-GALACTOSIDASE GENE

[75] Inventors: Mary E. Brawner, Wayne; Thomas G. Eckhardt, Collegeville; Louis R. Fare, Laffayette Hill, both of Pa.

[73] Assignee: SmithKline Beckman Corporation, Philadelphia, Pa.

[21] Appl. No.: 681,749

[22] Filed: Dec. 14, 1984

Related U.S. Application Data

[63] Continuation-in-part of Ser. No. 586,536, Mar. 5, 1984, abandoned, which is a continuation-in-part of Ser. No. 384,650, Jun. 3, 1982, abandoned.

[51] Int. Cl.⁴ ............... C12N 15/00; C12N 1/20; C12N 1/00; C07H 15/12
[52] U.S. Cl. ............... 435/253; 435/172.3; 435/886; 435/320; 536/27; 935/14
[58] Field of Search ............... 435/172.3, 253, 317; 536/27; 935/14

[56] References Cited

U.S. PATENT DOCUMENTS 3,816,259  6/1974  Collinge et al. ............... 435/207

FOREIGN PATENT DOCUMENTS 2033905  5/1980  United Kingdom .

OTHER PUBLICATIONS

Stuber et al., PNAS, vol. 78, pp. 167–171, Jan. 1981.
Sancar et al., Cell, vol. 28, pp. 523–530, Mar. 1982.
Ribb et al., Nature, 284:526–531, (1980).
Thompson et al., Nature, 286:525–527, (1980).
Davis et al., Nature, 283:433–438, (1980).
Villa-Komaroff et al., Proc. Nat'l Acad. Sci., U.S.A., 75:3727–3731, (1978).
Vining, L. C. and Chatterjee, S. Hradec Kralova, Czechoslovakia, Aug. 1981, London, Academic Press, Nov. 1982, pp. 35–46.
Sanchez, J. et al., Experientia 37(5):469, 1981.
Foster, J. W. and Katz, E. J. Bacteriol. 148(2):670–677, 1981.
Chatterjee, S. and Vining, L. C. Can J. Microbiol 28(3):311–317, 1982.
Sanchez, J. and Hardisson C. Can J. Microbiol 25(7):833–840, 1979.
Sanchez, J. and Hardisson C. Curr. Microbiol. 4(2):91–94, 1980.
T. Eckhardt and L. Fare, GIM Meeting 1982, Kyoto, Japan.
D. Taylor, T. Eckhardt, and L. Fare, Biochem Engineering III, 1982, Santa Barbara, Calif.
W. Burnett, M. Brawner, D. Taylor, L. Fare, J. Fanelli, T. Eckhardt, and M. Rosenberg 84:107, ASM Meeting, 1983.
T. Eckhardt, L. Fare, M. Brawner, D. Taylor, M. Rosenberg, J. Henner and W. Burnett, ASM Meeting on Membrane Assembly and Protein Export, 1985, South Bend, Ind.
L. Fare, J. Strickler, M. Rosenberg and T. Eckhardt, Conference on Expression of Foreign Genes, 1985, Rensselaerville, N.Y.
D. Taylor, T. Eckhardt and L. Fare, Ann. N.Y. Acad. Sci. 413, 47–56.
W. Burnett, M. Brawner, D. Taylor, L. Fare, J. Henner, T. Eckhardt in Microbiology 1985, 441–444, L. Levin, Ed. ASM Publications, Washington, D.C.

Primary Examiner—Alvin E. Tanenholtz
Attorney, Agent, or Firm—Edward T. Lentz; Janice E. Williams; Alan D. Lourie

[57] ABSTRACT

A DNA fragment from Streptomyces sp. which contains a gene which can code for an excretable protein is isolated, inserted into a plamid vector and used to transform other Streptomycetes.

21 Claims, 1 Drawing Figure

CLONED STREPTOMYCETE LIVIDANS EXCRETABLE β-GALACTOSIDASE GENE

This is a continuation-in-part of U.S. patent application Ser. No. 586,536, filed Mar. 5, 1984, now abandoned which is a continuation-in-part of U.S. patent application Ser. No. 384,650, filed June 3, 1982 now abandoned.

FIELD OF THE INVENTION

This invention relates to the field of biotechnology, specifically to genetic engineering. More particularly, the invention relates to the cloning of the gene coding for β-galactosidase from a Streptomyces species onto suitable vectors, expression of such cloned gene in other Streptomyces species, the method of detecting and identifying such gene by monitoring the β-galactosidase which is excreted into the growth medium and the use of such cloned gene for various genetic engineering purposes.

BACKGROUND INFORMATION

Although the Actinomycetales produce more than half of the known antibiotics having valuable clinical and other applications as secondary metabolites and, thus, are recognized as a key target for application of gene manipulation techniques, many problems remain to be overcome before specific useful genes are successfully identified and cloned ["Molecular Breeding and Genetics of Applied Microorganisms", Sakaguchi and Okanishi, eds., Academic Press (New York) Kodansha Ltd. (Toyko) 1980, pgs. 130–131]. Until the present work, cloning of a β-galactosidase gene from a Streptomyces species onto a suitable vector followed by introduction and expression of such vector has not been reported. Prior work has concerned development of other cloning systems or vectors for Streptomycetes [Bibb et al. (1978), Nature 274: 398–400; Hayakawa et al. (1979), J. Antibiot. XXXII(12): 1348–1350; Okanishi et al. (1980), J. Antibiot. XXXIII(1): 88–91; Bibb et al. (1980), Nature 284: 526–531; Thompson et al. (1980), Nature 286: 525–527; Suarez et al. (1980), Nature 286: 527–529; Bibb et al. (1981), Mol. Gen. Genet. 184: 230–240]; [Bibb (1981), "Microbiology-1981", Schlessinger, ed., American Society for Microbiology, (Washington, D.C.) 1981, pgs. 367–370 and Hopwood et al. (1981), "Microbiology-1981", supra. pgs. 376–379], cloning and expression in Streptomyces sp. of genes derived from Escherichia coli [Schottel et al. (1981), J. Bacteriol. 146: 360–368] and cloning of genes from Streptomycetes in Escherichia coli ["Molecular Breeding and Genetics of Applied Microorganisms", supra; pgs. 130–137]. Chater et al. (1982), Current Topics in Microbiol. and Immunol. 96: 69–95, review gene cloning in Streptomyces and is incorporated by reference herein as though fully set forth.

Work with various β-galactosidase genes, their expression and application of such expression as an assay or detection method has been reported by Rose et al. (1981), Proc. Natl. Acad. Sci. USA 78(4): 2460–2464, for expression in yeast of yeast genes fused to β-galactosidase genes from Escherichia coli; by Casadaban et al. (1980), J. Mol. Biol. 138: 179–207, for fusion of β-galactosidase genes to promoters in Escherichia coli and assay following transformation; and by Talmadge et al. (1981), Nature 294: 176–178, for construction of Escherichia coli containing a plasmid encoding a β-galactosidase-preproinsulin fusion protein.

Collinge et al., U.S. Pat. No. 3,816,259, disclose that a Streptomyces coelicolor preparation had a β-galactosidase activity.

In general, the activity of promoters can be assayed by measuring the amount of gene product which is formed as a consequence of transcription starting from a specific promoter. The amount of gene product formed is determined by using a specific property of that gene product, such as enzymatic activity. In studying gene expression or in constructing high expression vectors which rely on highly efficient promoters, the gene which is naturally expressed from such a promoter is replaced by the structural gene whose product can be more easily monitored. The lacZ gene from Escherichia coli [Casadaban et al. (1980), supra.] is frequently used for this purpose.

A variety of chromogenic substrates, such as 5-bromo-4-chloro-3-indolyl-β-D-galactosidase (referred to as "X-gal") or o-nitrophenyl-β-D-galactoside (referred to as "ONPG") can be used to monitor enzymatic activity as described by Miller (1972), "Experiments in Molecular Genetics", Cold Spring Harbor Laboratories (Cold Spring Harbor, N.Y.). These substrates are advantageous since the efficiency of a promoter fused to a gene coding for an enzyme which can react with the substrate, such as the lacZ gene, can be monitored by growing the organism on a solid agar medium containing the substrate and observing for enzyme-substrate reaction. In this manner, several hundred individual colonies can be scored at one time for their ability to express the gene. Thus, relatively rare events such as the occurrence of a highly efficient promoter can be detected. β-Galactosidase expression can be used in such a procedure to assay gene transcription and to detect and isolate mutants which over-produce a particularly desired protein, such as an enzyme involved in antibiotic production.

In order to effectively use such a powerful approach as described above, it is crucial that the chosen substrate has the opportunity to react with the enzyme. If, as in the case of β-galactosidase produced by Escherichia coli, the enzyme is intracellular, the substrate must enter the cell in order for the enzyme-substrate reaction to occur. With Streptomyces lividans, however, the commonly used substrates, X-gal and ONPG, enter the cell only poorly as verified by comparing the intracellular β-galactosidase activity of a suitable organism with dye formation on plates. For example, we have found that although intracellular activity as measured with cell extracts and with ONPG as substrate was very high (300 nmoles/mg protein/min), no significant color reaction with whole cells and with either ONPG or X-gal was found. Furthermore, Actinomycetes differ from many other microorganisms by the formation of an aerial mycelium which separates the cells physically from the substrate, thus further restricting access of the substrate to the cells [Kalakoutskii et al. (1976), Bacteriol. Rev. 40(2): 469–524].

SUMMARY OF THE INVENTION

The invention lies in the discovery that certain strains of Streptomyces sp. naturally produce an excretable β-galactosidase, herein referred to as the Streptomyces β-galactosidase. The enzyme is useful for degradation of certain β-galactosides, such as lactose, and can be used as a diagnostic or laboratory reagent. The enzyme of the invention is free of naturally occurring contaminants because it is partially or fully purified or because it is produced by a heterologous host or by other nonnatural processes.

Another aspect of the invention is a DNA fragment containing the Streptomyces β-galactosidase gene. The gene can be readily expressed in a variety of Streptomycetes by inserting it onto a suitable vector. The DNA fragment contains at least the nucleotide sequence which causes expression of the excretable β-galactosidase. Other nucleotides, including for example, promoter sequences, from the donor organism or other sources, can also be present.

Another aspect of the invention is a DNA fragment containing the promoter of the Streptomyces β-galactosidase gene, not linked to the Streptomyces β-galactosidase gene.

Another aspect of the invention is a DNA fragment containing the coding sequence of the Streptomyces β-galactosidase gene, not linked to the Streptomyces β-galactosidase gene promoter.

Another aspect of the invention is a fused gene comprising an excretion signal from the gene of the invention, that is, the whole coding sequence or a portion thereof, fused to a heterologous coding sequence.

Other aspects of the invention include vectors containing said fragments and microorganisms transformed therewith.

All of these embodiments of the invention, as well as others described herein, are readily attainable uses of this invention and are considered as further aspects of the same invention.

DISCLOSURE OF THE INVENTION

Figure 1:
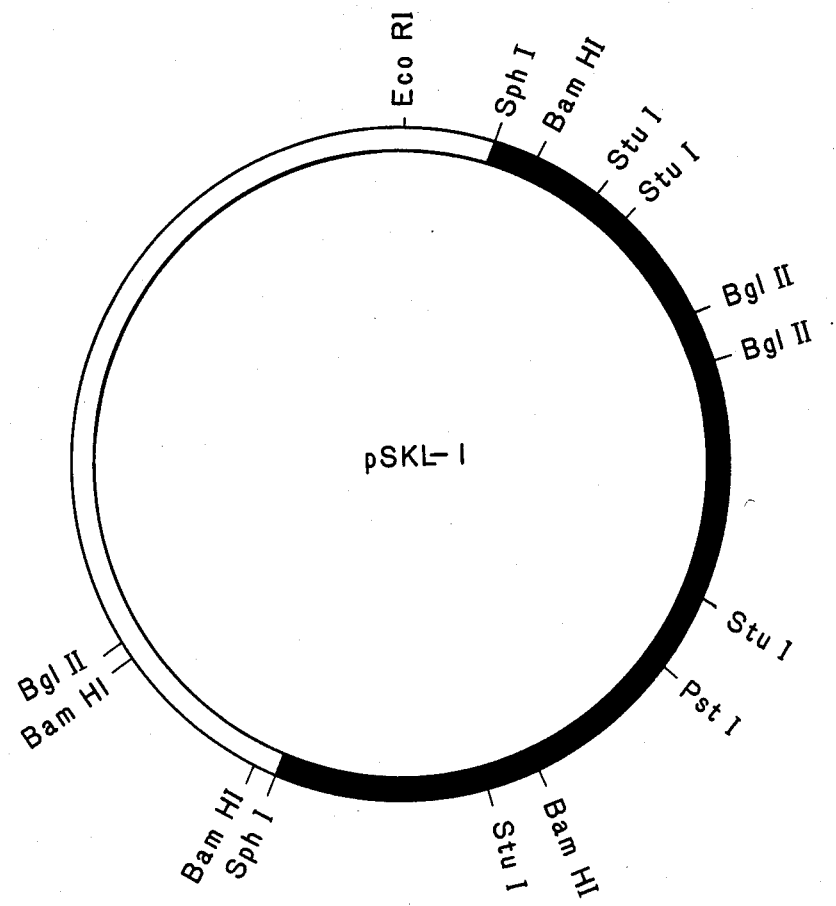
FIG. 1 is a restriction endonuclease cleavage map of pSKL-1.

Described below are various DNA fragments of Streptomyces origin which have been discovered to contain a gene which can cause expression of an excreted β-galactosidase. It is possible that the product of the gene of the invention is something other than the excreted β-galactosidase. For example, the product of the gene may be a regulatory protein which activates a β-galactosidase pathway. In any event, because expression of the gene of the invention results in production of the Streptomyces β-galactosidase in hosts which do not normally produce measurable levels of β-galactosidase, the gene is herein referred to as the Streptomyces β-galactosidase gene.

It is appreciated that derivatives of the fragments disclosed herein may also result in expression of the Streptomyces β-galactosidase or of a related polypeptide, i.e., one which has the β-galactosidase activity. Such derivatives, which are included within the invention, include, for example truncated fragments and fragments differing by a substitution, addition or deletion of one or more deoxyribonucleotides, including, perhaps, one or more restriction enzyme sites, which differences do not materially affect the β-galactosidase activity of resulting products.

The DNA fragments of the invention are recombinant DNA molecules, that is, DNA sequences, single or double stranded, that have been isolated from the larger molecules in which they are naturally present, such as chromosomal DNA, or from their natural hosts, or which have been partially or wholly synthesized, and which may be fused to other DNA fragments, such as to form expression units or cloning or expression vectors.

The Streptomyces β-galactosidase gene expression unit was originally isolated on a 16 kb Sph I region of chromosomal DNA of S. lividans strain 1326. The 16 kb Sph I region has been mapped as follows:

| Restriction Enzyme | Location (kb) |
|---|---|
| Sph I | 0 |
| Bam HI | 0.6 |
| Pvu II | 0.9 |
| Bal I | 1.3 |
| Stu I | 1.5 |
| Sal I | 1.8 |
| Stu I | |
| Bcl I | |
| Bgl II | 2.7 |
| Bgl II | 3.7 |
| Pvu II | 5.7 |
| Nru I | 6.5 |
| Pvu II | 7.2 |
| Bcl I | |
| Stu I | 7.7 |
| Pst I | 8.8 |
| Bal I | 8.0 |
| Pvu II | 10.3 |
| Pvu II | 10.9 |
| Bam HI | 11.6 |
| Stu I | 12.0 |
| Pvu II | 13.7 |
| Sph I | 15.5 |

This table will be used for further references herein to DNA fragments naturally present within the Sph I region. So, for example, the 1.0 kb Bgl II (2.7)-Bgl II (3.7) fragment will be referred to as such whether or not there are additional deoxyribonucleotides upstream and/or downstream thereof.

The indicated locations are approximate. Also, other sites for the same or other restriction enzymes may also be present. For example, the Pst I (8.8)-Bam HI (11.6) region within the 7 kb Pst I-Sph I region has been further mapped as follows:

| Restriction Enzyme | Location (kb) |
|---|---|
| Pst I | 8.8 |
| Sma I/Ava I | 8.9 |
| Sma I/Ava I | |
| Xmn I | 9.9 |
| Ava I | |
| Pvu II | 10.3 |
| Sma I/Ava I | |
| Pvu II | 10.9 |
| Bam HI | 11.6 |

The entire gene expression unit can be obtained by restricting chromosomal DNA with Sph I, or with Pst I and Sph I and selecting for the Pst I (8.8)-Sph I (15.5) fragment. It, or other fragments of this region of chromosomal DNA, can be cloned in a vector, such as a phage or plasmid, by known techniques. Alternatively, by way of example, all or part of the gene expression unit can be sequenced and parts thereof can be synthesized. These can be used directly as regulatory or coding sequences or to construct other fragments such as hybrid promoters or hybrid coding sequences or to probe for similar regions in other organisms by standard hybridization techniques.

A transcription start site has been identified about 300 bases upstream (3') of the Xmn I (9.9) site based on results of S1 mapping. This appears to be the transcription start site of the Streptomyces β-galactosidase gene.

A promoter region, including the transcription start site, can be isolated from the Pst I (8.8)-Xmn I (9.9) region by restriction with Pst I and Xmn I. The promoter isolated on this fragment is referred to as the P3 promoter. Such fragment carrying the P3 promoter can be cut back from the 3' and 5' ends to remove nonessential sequences to prepare a P3 fragment having a translation start site, a Shine-Dalgarno sequence, and/or a transcription initiation site. Removal of a large number of 5' non-coding sequences reduces promoter efficiency. For expressing heterologous proteins from non-Streptomycetes, it may prove desirable to include a N-terminal coding sequence of Streptomyces origin, such as the N-terminal portion of the Streptomyces β-galactosidase coding sequence which sequence can be useful in transport of the protein to or beyond the membrane.

The Streptomyces β-galactosidase coding sequence can similarly be isolated on a Pst I (8.8)-Sph I (15.5) fragment. Insertion of translation stop codons into the Stu I (12.0) site resulted in loss of β-galactosidase activity. Sequences near the 5' end of the coding region appear to be involved in excretion. Such sequences can be isolated by known techniques such as disclosed by Silhavy et al., U.S. Pat. No. 4,336,336 for fusion to heterologous, that is, non-Streptomyces β-galactosidase, coding sequences for proteins which are normally not excreted and linked in phase to a promoter for expression of an excreted fusion protein.

In an illustrative procedure, Streptomyces lividans strain 1326 [National Collection of Industrial Bacteria, Aberdeen, Scotland, number 11416; Bibb et al., (1981), Mol. Gen. Genetics 184: 230-240; Krasilnikov et al., "The Biology of Certain Groups of Actinomycetes", Krasilnikov, ed., Science Press (Moscow) 1965, pgs. 109-110, which contains a gene which codes for β-galactosidase which is naturally excreted in its original strain, is collected by standard techniques, such as the technique described by Chater et al., supra.] A DNA fragment containing the Streptomyces β-galactosidase gene is isolated by treating the DNA with a restriction endonuclease. If the enzyme-substrate reaction yields a poorly diffusible dye, enzymatic activity can be monitored by the formation of a halo of colored dye around a producing colony on an agar plate when assaying by this procedure. The preferred chromogenic substrate is X-gal because the product is such a poorly diffusible dye. The sensitivity of this procedure is such that one producing colony among 300 to 500 colonies can be identified on a single petri dish (90 mm diameter).

The gene isolated as described above, and which originated from Streptomyces, can be readily expressed in other species of Streptomyces such as *Streptomyces griseus, Streptomyces aureofaciens, Streptomyces fradiae, Streptomyces niveus* and others as well as other microorganisms. Suitable hosts can be selected by known, routine procedures comprising coloning the gene in a given host and selecting for β-galactosidase activity as described herein. *Streptomyces lividans, Streptomyces albus* and *Streptomyces griseus* are the preferred host species.

A variety of vectors are useful in this invention, the choice of an advantageous one being within the ken of one skilled in the relevant art. Examples of usable vectors are plasmids pIJ6 [Thompson et al. (1980), Nature 286: 525-527], pIJ101 [Chater et al. supra] and others which are capable of replicating in the ultimate host strain and permit facile selection for the presence of the vector in such strain. Likewise, various standard growth media can be employed. The plasmid, pIJ6, is the preferred vector.

Incorporation of a plasmid vector containing the desired DNA fragment into microorganisms can be accomplished by usual transformation methods, although other procedures such as transduction or conjugation may be used with suitable hosts. Such procedures are described in and known to the art.

The following examples are intended to provide a detailed description of the present invention and manner of carrying it out, but not to limit its scope, applicability or utility.

EXAMPLE 1

Chromosomal DNA from *Streptomyces lividans* strain 1326 [Bibb et al. (1981), supra.] was isolated using the procedure described by Chater et al, supra. Plasmid pIJ6 isolated from *Streptomyces lividans* [Thompson et al. (1980), supra.] was used as the cloning vector as this plasmid carries the gene for thiostrepton resistance, which is useful as a selective marker to select for the plasmid in a given thiostrepton sensitive strain such as 1326 and its derivatives. Treatment of the chromosomal DNA and the pIJ6 DNA with Sph I restriction endonuclease or Pst I restriction endonuclease yielded DNA fragments having a protruding complementary 3' DNA sequence. The pIJ6 DNA was additionally treated with alkaline phosphatase to prevent regeneration of the cloning vector without an additional DNA insert. The Sph I and the Pst I generated DNA's (5 ug of chromosomal DNA, 1 ug of pIJ6 DNA) were ligated separately at 16° C. for 7 days using standard procedures. The ligated DNA's were transformed substantially according to the procedure described by Chater et al., supra., using about $2 \times 10^7$ protoplasts derived from *Streptomyces lividans* strain 1326-9, a nitrosoguanidine induced mutant of strain 1326 lacking any excreted β-galactosidase activity. The protoplasts were spread onto regeneration medium plates and incubated for 18-24 hours at 28° C. The plates were overlaid with a soft agar mixture (0.4% agar in water) containing 100 ug/ml of thiostrepton to select for transformed offspring and 150 ug/ml of X-gal. The plates were incubated for another 2 to 6 days at 28° C., then scored for the appearance of characteristic blue colonies.

Of over 10,000 thiostrepton resistant colonies resulting from the Sph I cloning, 9 turned blue; from about the same number of colonies resulting from the Pst I cloning, one turned blue. The plasmid DNA of all the blue colonies was isolated and analyzed.

Both plasmid DNA from the Sph I and the Pst I cloning had a common region derived from the chromosome and not previously present on the pIJ6 plasmid. Initially, it was believed, based on what was believed to be the structur of PIJ6, that said region contained the Streptomyces β-galactosidase gene. The total Sph I insert was believed to comprise only about 10 kb. As shown in further examples below, it was subsequently discovered that although the gene is located on the Sph I insert, the common region is the 7 kb Pst I (8.8)-Sph I (15.5) region.

A 32 kilobase plasmid derived from the Sph I cloning was termed "pSKL-1". Cleavage by the restriction endonucleases was carried out in the standard manner. The plasmid derived from the Pst I cloning was termed "pX". pSKL-1 is represented by the restriction endonuclease cleavage map show in FIG. 1.

The isolated plasmid DNA from pSKL-1 was used to transform *Streptomyces lividans* 1326-9. Over 70% of the thiostrepton resistant offspring showed an excreted β-galactosidase activity, indicating the presence and expression of the gene on the plasmid. The enzyme levels of cell extracts of the pSKL-1 transformed strain, strain 1326-9/pSKL-1, were increased, in some cases, 100 times, thus showing the presence of the gene on the plasmid. Results of one experiment are given in Table 1, below.

TABLE 1

| STRAIN | β-GALACTOSIDASE ACTIVITY (nmoles/mg protein/min) CARBON SOURCE IN GROWTH MEDIUM | | |
|---|---|---|---|
| | GLUCOSE | LACTOSE | GALACTOSE |
| 1326 | 12 | 76 | 184 |
| 1326-9 | 7 | 24 | 302 |
| 1326-9/pSKL-1 | 372 | 843 | 1242 |

As indicated in Table 1, a few 1326-9 cultures produced more unexcreted β-galactosidase in the presence of galactose than some 1326 cultures.

Transformants harboring the pSKL-1 plasmid produced darker blue colonies than the original 1326 strains, demonstrating the utility of the DNA fragment containing the β-galactosidase gene in the construction of high expression vectors.

β-galactosidase expression from a plasmid is less stable in strain 1326-9 than in strain 1326. This is believed to be due to recombination with chromosomal DNA.

EXAMPLE 2

Plasmid pSKL-1 was also transformed into *Streptomyces griseus* strain BC6, ATCC No. 10137, a strain which naturally does not possess an excreted β-galactosidase, by the above described procedures. The offspring of strain BC6 containing pSKL-1 (strain BC6/pSKL-1), however, produced the Streptomyces β-galactosidase. pSKL-1 was also transformed into *Streptomyces albus*, which is naturally deficient in β-galactosidase activity. Resulting transformants produced the Streptomyces β-galactosidase. These results show the applicability and usefulness of the Streptomyces β-galactosidase promoter and coding sequence in other Streptomycete hosts.

EXAMPLE 3

A pSKL-1 derivative identified as pSKL-4 was isolated as a spontaneous deletion of pSKL-1. pSKL-4 comprised the 7 kb Pst I-Sph I fragment but was deleted in most, about 8.5 kb, of the chromosomal DNA upstream of the Pst I site. pSKL-4 was transformed into *Streptomyces albus*, which is naturally deficient in β-galactosidase activity. The resulting transformants produced the Streptomyces β-galactosidase with similar results as were obtained with the pSKL-1 transformants of Example 2, above.

EXAMPLE 4

The Bgl II fragment was deleted from pSKL-1 to prepare pBB2B. The plasmid, pBB2B, is identical to pSKL-1 except for the deletion of the Bgl II fragment. *S. lividans* 1326 was transformed with pBB2B and its β-galactosidase excretion after 14 hours and 24 hours was compared with that of a 1326 strain transformed with pSKL-1. Results were as shown in Table 2, below.

TABLE 2

| | β-GALACTOSIDASE ACTIVITY (nmoles/mg cells/min) (CARBON SOURCE: GALACTOSE) | |
|---|---|---|
| STRAIN | 14 h | 24 h |
| 1326/pSKL-1 | .03 | .06 |
| 1326/pBB2B | .002 | .12 |

Supernatant from the 1326/pSKL-1 culture contained the Streptomyces β-galactosidase as shown by activity and protein polyacrylamide gel electrophoresis. Supernatant from the 1326/pBB2B culture did not.

*Streptomyces lividans* strains 1326 and 1326-9 and a strain containing pIJ6 are publicly available from various sources. To further ensure availability, these strains have been deposited with the Agricultural Research Culture Collection in Peoria, Ill. on June 1, 1982, without restrictions on availability, and assigned accession numbers 15091, 15090 and 15092, respectively.

While the above description is illustrative of the invention and of the preferred embodiments thereof, the invention is not limited to the precise embodiments illustrated herein, but rather includes all modifications thereof coming within the scope of the following claims. In particular, the invention is not limited to fragments having restriction endonuclease sites or DNA sequences as illustrated, inasmuch as such sites and sequences can vary or be varied without materially affecting the invention.

What is claimed is:

1. An isolated DNA fragment containing the Streptomyces β-galactosidase gene *Streptomyces lividans*.

2. A DNA fragment of claim 1 comprising the 16 kb Sph I region of *Streptomyces lividans* chromosomal DNA.

3. A DNA fragment of claim 2 comprising the 7 kb Pst I-Sph I region of *Streptomyces lividans* strain 1326 chromosomal DNA.

4. A vector containing the DNA fragment of claim 1.

5. The vector of claim 4 which is plasmic pSKL-1.

6. A microorganism transformed with the vector of claim 4.

7. The microorganism of claim 6 which is a Streptomyces.

8. The microorganism of claim 7 which is *S. lividans* strain 1326-9/pSKL-1.

9. The microorganism of claim 7 which is *S. lividans* strain BC6/pSKL-1.

10. A DNA fragment containing the promoter of the Streptomyces β-galactosidase gene, of *Streptomyces lividans* not linked to the Streptomyces β-galactosidase structural gene.

11. A vector containing the promoter fragment of claim 10.

12. A microorganism transformed with the vector of claim 11.

13. The microorganism of claim 12 which is a Streptomyces.

14. A DNA fragment containing the coding sequence of the Streptomyces β-galactosidase gene, of *Streptomyces lividans* not linked to the Streptomyces β-galactosidase gene promoter.

15. A vector containing the DNA fragment of claim 14.

16. A microorganism transformed with the vector of claim 15.

17. The microorganism of claim 16 which is a Streptomyces.

18. A fused gene comprising the nucleotide sequence of the Streptomyces β-galactosidase gene of *Streptomyces lividans* which causes excretion of the β-galactosidase fused to a heterologous coding sequence.

19. A vector containing the fused gene of claim 18 linked in phase to a promoter.

20. A microorganism transformed with the vector of claim 19.

21. The microorganism of claim 20 which is a Streptomyces.

* * * * *